United States Patent [19]

Janusz et al.

[11] Patent Number: 4,532,139
[45] Date of Patent: Jul. 30, 1985

[54] COMPOUNDS AND COMPOSITIONS USEFUL FOR PRODUCING ANALGESIA

[75] Inventors: John M. Janusz, Fairfield; Thomas R. LaHann, Cleves, both of Ohio

[73] Assignee: The Procter & Gamble Company, Cincinnati, Ohio

[21] Appl. No.: 514,204

[22] Filed: Jul. 14, 1983

[51] Int. Cl.$^3$ .................. A01N 37/22; C07C 103/133
[52] U.S. Cl. .................... 514/627; 564/207; 564/74; 514/546; 514/599
[58] Field of Search .................. 564/74, 207; 424/320, 424/321, 335

[56] References Cited

U.S. PATENT DOCUMENTS

| | | | |
|---|---|---|---|
| 2,710,299 | 6/1955 | Kottler et al. | 564/207 X |
| 2,845,449 | 7/1958 | Toland | 564/74 X |
| 3,024,281 | 3/1962 | Parris | 564/207 X |
| 3,108,038 | 10/1963 | Fielding et al. | 564/207 X |
| 3,120,434 | 2/1964 | Pohland | 564/74 X |
| 3,167,556 | 1/1965 | Krapcho | 564/207 X |
| 3,192,213 | 6/1965 | Krapcho | 564/207 X |
| 3,201,401 | 8/1965 | Krapcho | 564/207 X |
| 3,504,028 | 3/1970 | Beregi et al. | 564/207 X |
| 3,780,103 | 12/1973 | Knell | 564/207 X |
| 4,031,186 | 6/1977 | de Benneville | 564/74 X |
| 4,244,730 | 1/1981 | Kobzina | 564/74 X |
| 4,372,972 | 2/1983 | Chan | 564/207 X |

Primary Examiner—Paul F. Shaver

Attorney, Agent, or Firm—David L. Suter; David K. Dabbiere; Steven J. Goldstein

[57] ABSTRACT

Alkynamide compounds, and pharmaceutically-acceptable salts thereof, of the formula:

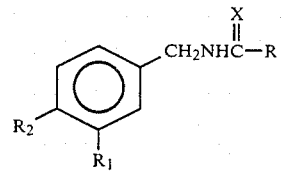

wherein X is O or S; R is straight or branched alkyne having from 11 to 23 carbon atoms; $R_1$ is H, OH, or $OCH_3$; $R_2$ is OH or a short-chain ester; and wherein at least one of $R_1$ and $R_2$ is OH or $OCH_3$. Compositions, useful for producing analgesia in humans or lower animals, comprise a safe and effective amount of: an alkynamide, pharmaceutically-acceptable salts thereof, or mixtures thereof; and a pharmaceutically-acceptable carrier. Preferably, these alkynamides are N-vanillylalkynamides. Methods of treatment, comprising administering a safe and effective amount of these alkynamides, pharmaceutically-acceptable salts thereof, or mixtures thereof, include methods of parenteral, oral, and topical administration.

19 Claims, No Drawings

COMPOUNDS AND COMPOSITIONS USEFUL FOR PRODUCING ANALGESIA

BACKGROUND OF THE INVENTION

This invention relates to compositions, containing certain N-phenylmethylalkynamides, having analgesic activity.

While "pain" is incapable of precise definition due to its basically subjective nature, it can generally be said that the term refers to feelings of distress or suffering caused by stimulation of specialized nerve endings. A great variety of drugs have been developed to reduce pain in man and other animals; some directed to eliminating pain at its source, and others directed to blocking the assimilation of pain by the brain. Among the latter group of drugs that are designed to block the sensation of pain, are the analgesics, which generally relieve pain without causing unconsciousness. Analgesics can be further classified in two main categories: opioid analgesics, including morphine, codeine, levorphanol, and the morphine-like analgesics meperidine, and methadone; and antipyretic analgesics, such as aspirin, phenacetin, acetaminophen, phenylbutazone, and indomethacin.

Although the precise pharmacological action of these analgesics is uncertain, there are certain effects which readily distinguish the opoid analgesics from the antipyretics. In particular, the antipyretics are weak analgesics, which much of their effect in the peripheral nervous system, so that behavioral changes do not usually occur. Generally, these analgesics relieve only somatic pain originating from muscles, joints, tendons and fasciae, and are ineffective against deep visceral pain. However, the opioid analgesics are quite effective against all types of pain, with broad based action in the central nervous system. Aside from potent analgesia, the opioids, also known as narcotics, often produce effects on mood and other behavioral changes. Perhaps the most notable side effect of the opioid analgesics is the fact that their repeated use is associated with tolerance as well as psychic and physical dependence.

It has been recently discovered that capsaicin, a natural product of certain species of the genus Capsicum, induces analgesia in animals. Capsaicin (8-methyl-N-vanillyl-6E-nonenamide) and "synthetic" capsaicin (N-vanillylnonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al., *Science*, 206, 481–483 (1979). The use of capsaicin to prevent dipilatory irritation is also disclosed in U.S. patent application Ser. No. 330,731, LaHann, et al., filed Dec. 14, 1981.

Specifically, capsaicin prevents the development of cutaneous hyperalgesia and also provides relief of deep visceral pain and severe pain. In certain tests, capsaicin produces a level of analgesia comparable to morphine, yet it is not antagonized by such narcotic antagonists as nalorphine and naloxone. Thus, capsaicin does not appear to belong to either of the major categories of analgesics, described above.

Compounds structurally similar to capsaicin have been described in the chemical literature. These references, though, do not suggest analgesic activity for these compounds. For example, Newman, "Natural and Synthetic Pepper-Flavored Substances (6)," *Chemical Products*, 102–106 (1954) lists the relative pungency of approximately 164 compounds, including N-vanillyloleamide and other alkenamide derivatives of capsaicin. Ott and Zimmermann, *Liebigs Ann.*, 425, 314–337 (1921) discloses a synthesis for N-vanillyloleamide. A synthesis for N-vanillyllinoleamide is disclosed in Ferris, *Australian Commonwealth, Dep. Supply, Def. Stand. Lab.*, No. 89 (1966) (Chem. Abs. 67:22919).

U.S. Pat. No. 4,238,505, Nelson, issued Dec. 9, 1980, discloses 3-hydroxyacetanilide for use in producing analgesia in animals. U.S. patent application Ser. No. 359,464, LaHann, et al., filed Mar. 18, 1982, describes hydroxyphenylacetamides with analgesic and anti-irritant activity. Similarly, analgesic and anti-irritant activity is disclosed for N-vanillylsulfonamides in U.S. patent application Ser. No. 360,953, Buckwalter, et al., filed Mar. 23, 1982, now U.S. Pat. No. 4,401,663; N-vanillylureas in U.S. patent application Ser. No. 381,672, Buckwalter, et al., filed May 25, 1982, now U.S. Pat. No. 4,460,602; and N-vanillylcarbamates in U.S. patent application Ser. No. 384,685, Buckwalter, et al., filed June 3, 1982, now U.S. Pat. No. 4,434,473.

It has now been discovered that certain N-phenylmethyl alkynamides have analgesic activity in humans and lower animals. In particular, these alkynamides have potent analgesic activity similar to that of capsaicin, but are substantially less toxic.

SUMMARY OF THE INVENTION

The present invention provides compounds useful for producing analgesia in humans and lower animals, of the formula:

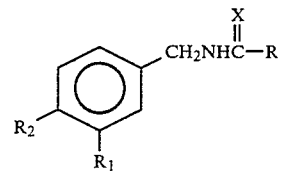

wherein X is O or S, R is straight or branched alkyne having from 11 to 23 carbon atoms, $R_1$ is H, OH, or $OCH_3$, $R_2$ is OH or a short-chain ester, and wherein at least one of $R_1$ and $R_2$ is OH or $OCH_3$; and pharmaceutically-acceptable salts thereof.

This invention also provides compositions comprising a safe and effective amount of these compounds, or mixtures thereof, and a pharmaceutically-acceptable carrier. Also provided are methods for producing analgesia by administering the compounds and compositions of this invention.

DESCRIPTION OF THE INVENTION

The compositions and methods of this invention incorporate certain N-[(substituted phenyl)methyl]alkynylamides (e.g., N-vanillyl-alkynylamides), or pharmaceutically-acceptable salts thereof, (herein "alkynamides") of the formula:

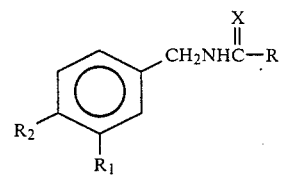

wherein X is O or S; R is straight or branched alkyne having from 11 to 23 carbon atoms; $R_1$ is H, OH or $OCH_3$; $R_2$ is OH or a short-chain ester; and wherein at least one of $R_1$ and $R_2$ is OH or $OCH_3$. R preferably contains from 16 to 21 carbon atoms and, preferably, the unsaturated bonds are at position six or greater, i.e., wherein R is a (n-alkyne), n is at least six. Also preferred are alkynamides wherein X is O, alkylnamides wherein $R_1$ is $OCH_3$ and $R_2$ is OH, and alkylnamides wherein $R_2$ is a short-chain (i.e., $C_1$-$C_6$) ester, e.g., acetoxy.

A preferred alkynamide is N-vanillyl-9-octadecynamide. Preferred pharmaceutically-acceptable alkylnamide salts include the sodium, potassium, calcium, magnesium, and ammonium salts.

The alkynamides described herein can be readily prepared by the following general synthetic scheme:

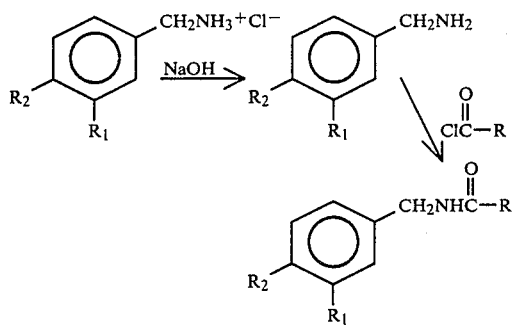

COMPOSITIONS

The compositions of the present invention comprise:
(a) a safe and effective amount of an alkynamide; and
(b) a pharmaceutically-acceptable carrier.

A safe and effective amount of alkynamide is that amount which provides analgesia, thereby alleviating or preventing the pain being treated at a reasonable benefit/risk ratio, as is intended with any medical treatment. Obviously, the amount of alkynamide will vary with such factors as the particular condition that is being treated, the severity of the condition, the duration of the treatment, the physical condition of the patient, the nature of concurrent therapy (if any), the specific formulation and carrier employed, and the solublity and concentration of alkylnamide therein.

Depending upon the particular route of administration, a variety of pharmaceutically-acceptable carriers, well known in the art, may be used. These include solid or liquid fillers, diluents, hydrotropes, surface-active agents, and encapsulating substances. The amount of the carrier employed in conjunction with the alkynamide is sufficient to provide a practical quantity of material per unit dose of analgesic.

Pharmaceutically-acceptable carriers for systemic administration, that may be incorporated into the compositions of this invention, include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Specific pharmaceutically-acceptable carriers are described in the following U.S. patent applications, all incorporated by reference herein: Ser. No. 359,464, LaHann, et al., filed Mar. 18, 1982; Ser. No. 360,953, Buckwalter, et al., filed Mar. 23, 1982; Ser. No. 381,672, Buckwalter, et al., filed May 25, 1982; and Ser. No. 384,685, Buckwalter, et al., filed June 3, 1982. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50% of the alkynamide. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents. Preferred carriers for oral adminstration include gelatin, propylene glycol, cottonseed oil and sesame oil. Specific examples of pharmaceutically-acceptable carriers and excipients that may be used to formulate oral dosage forms, which may be used in formulating oral dosage forms containing alkynamides, are described in U.S. Pat. No. 3,903,297, Robert, issued Sept. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated by reference herein.

The compositions of the present invention can also be administered topically to a biologic subject, i.e., by the direct laying on or spreading of the composition on epidermal or epithelial tissue. Such compositions include lotions, creams, solutions, gels and solids. These topical compositions comprise a safe and effective amount, usually at least about 0.5%, and preferably from about 1% to about 2%, of the alkynamide. Suitable carriers for topical administration of the alkynamide preferably remain in place on the skin as a continuous film and resist being washed off easily by perspiration or by immersion in water. Generally, the carrier is organic in nature and capable of having dispersed or dissolved therein the alkynamide. The carrier may include pharmaceutically-acceptable emollients, emulsifiers, thickening agents, and solvents.

Specific systemic and topical formulations useful in this invention are described in the following U.S. patent applications, all incorporated by reference herein: Ser. No. 359,464, LaHann, et al., filed Mar. 18, 1982; Ser. No. 360,953, Buckwalter, et al., filed Mar. 23, 1982; Ser. No. 381,672, Buckwalter, et al., filed May 25, 1982; and Ser. No. 384,685, Buckwalter, et al., filed June 3, 1982. Topical vehicles, useful herein, are disclosed in the following U.S. patent applications, incorporated by reference herein: "Improved Penetrating Topical Pharmaceutical Compositions Containing 1-dodecylazacycloheptan-2-one", Ser. No. 506,275, Cooper, filed June 21, 1983; and "Penetrating Topical Pharmaceutical Compositions Containing N-(2-hydroxyethyl)-pyrrolidone", Ser. No. 506,273, Cooper, filed June 21, 1983. Additional formulations, useful for parenteral, oral, and topical administration of alkynamides, are disclosed in the following U.S. patent applications concurrently filed herewith, all incorporated by reference herein: "Compositions Useful for Producing Analgesia", Ser. No. 514,206, LaHann and Buckwalter; "Novel Compounds and Compositions Useful for Producing Analgesia", Ser. No. 514,207, LaHann, Janusz and Buckwalter; and Novel Compounds and Compositions Useful for Producing Analgesia", Ser. No. 514,208, Janusz, Buckwalter and LaHann.

METHODS FOR PRODUCING ANALGESIA

The present invention also encompasses methods of producing analgesia in humans or lower animals through administering, to the human or lower animal, a safe and effective amount, usually from about 1 mg to about 3600 mg per day, preferably from about 200 mg to about 2000 mg per day, of an alkynamide. While dosages higher than the foregoing are effective to produce analgesia, care must be taken in some individuals to prevent adverse side effects. The alkynamides and compositions of this invention can be used to treat and prevent pain, and to provide analgesia in various disorders at the deeper structures, muscles, tendons, bursa and joints associated with disease and trauma, and in various other conditions in which compounds such as aspirin, codeine, and morphine have heretofore been used to alleviate pain and discomfort.

The alkynamides and compositions of the instant invention can be administered topically or systemically. Systemic application includes any method of introducing the alkynamides into the tissues of the body, e.g., intrathecal, epidural, intramuscular, transdermal, intravenous, intraperitoneal, subcutaneous, sublingual, and oral administration.

A preferred method of parenteral administration is through intramuscular injection. As is known and practiced in the art, all formulations for parenteral administration must be sterile. For mammals, especially humans, (assuming an approximate body weight of 70 kg) individual doses of from about 2 mg to about 400 mg of alkynamide are acceptable. Individual doses of from about 50 mg to about 200 mg are preferred.

A preferred method of systemic application of the alkynamides is through oral administration. For mammals, especially humans, (assuming an approximate body weight of 70 kg) individual doses of from about 1 mg to about 900 mg of alkynamide are acceptable. Individual doses of from about 50 mg to about 600 mg are especially preferred.

Topical administration can be used to produce local or systemic analgesia, through directly laying on or spreading a safe and effective amount of the alkynamide, or composition containing an alkynamide, on epidermal or epithelial tissue, including outer skin and oral, gingival, and nasal tissue. The amount of alkynamide to be topically administered depends upon such factors as the sensitivity, type and location of tissue to be treated, the composition and carrier (if any) to be administered, and the particular alkynamide to be administered as well as the particular disorder to be treated and the extent to which systemic (as distinguished from local) analgesic effects are desired. The extent of systemic analgesia also depends upon such factors as the amount of alkynamide, the area of tissue to be covered, and the ability of the alkynamide composition to penetrate the skin tissues.

The following non-limiting Examples illustrate the compositions, processes, and uses of the present invention.

EXAMPLE I

N-vanillyl-9-octadecynamide was synthesized by the following method:

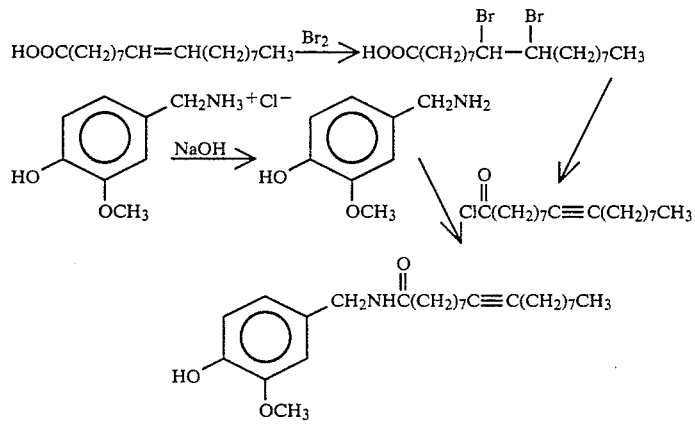

Specifically, 9-octadecenoic acid (oleic acid) (5 g) was dissolved in ether and chilled in a water bath, while stirring. Bromine was added, dropwise, allowing color to disappear after every four to five drops. When there was an excess of bromine (color remaining) the solvent and excess bromine were evaporated, yielding 8 g of 9,10-dibromooctadecanoic acid. A 30% solution of potassium hydroxide in ethylene glycol (13 ml) was added to this dibrominated oleic acid product, and refluxed at 185°–190° C. for six hours. The mixture was stirred overnight, then acidified with 10% HCl. The 9-octadecynoic acid (stearolic acid) was extracted into 100 ml petroleum ether, chilled, and the 4 g of resulting product crystals were filtered and dried. 15 ml of oxalyl chloride were added to 3.5 g of the stearolic acid product and the mixture refluxed for one hour. The excess oxalyl chloride was evaporated, yielding 9-octadecynyl chloride (stearoyl chloride)

2.4 g of 4-hydroxy-3-methoxybenzylamine-HCl was suspended in 35 ml of N,N-dimethylformamide (DMF), and stirred. Added were 5 ml of a 5N solution of NaOH, and the mixture was stirred for an additional 10 to 15 minutes. The DMF mixture was chilled in an ice bath, and the stearoyl chloride, prepared above and dissolved in ether, was added dropwise. The mixture was then stirred for 3 hours, allowing it to come to room temperature. The mixture was then poured into 300 ml water, layers separated, and the aqueous layer extracted with ethyl ether. The extracts were washed with HCl, sodium bicarbonate, water, and brine, and then dried and filtered. 5.3 g of crude N-vanillyl-9-octadecynamide was obtained. Purification by recrystallization from toluene and hexane, and then benzene and hexane, gave 2.8 g of analytically pure product. Its structure was confirmed via nuclear magnetic resonance and infrared spectroscopy.

In the above example, N-vanillyl-9-tetradecynamide, N-vanillyl-9-hexadecynamide, N-vanillyl-6-octadecynamide, N-vanillyl-11-octadecynamide, N-vanillyl-10-nonadecynamide, and N-vanillyl-13-docosynamide are each made by substituting the respective n-alkynoic acid for 9-octadecynoic acid in the above synthesis.

EXAMPLE II

An analgesic composition, according to the present invention, was made comprising:

| | |
|---|---|
| N—vanillyl-9-octadecynamide | 127.2 mg |
| ethanol | 0.3 ml |
| Tween 80 (polyoxyethylene 20 sorbitan mono-eleate) | 0.3 ml |
| Saline | 2.4 ml |

The composition was made by simple dissolution of the alkynamide in the liquid solvents. A mouse weighing 30 g, was injected subcutaneously with 0.2 ml of the composition, producing analgesia.

EXAMPLE III

A composition, according to the instant invention, for parenteral administration, is made with the following ingredients:

| | |
|---|---|
| N—vanillyl-10-nonadecynamide | 100 mg/ml of carrier |
| carrier (percent-by-weight): | |
| propylene glycol | 72% |
| polyethylene glycol | 17% |
| water | 10% |
| benzyl alcohol | 1% |

The alkynamide is dissolved in the carrier and a human subject, weighing 70 kg, is injected subcutaneously with 1.0 ml of the composition thereby prepared, producing analgesia. At eight-hour intervals, two more subcutaneous injections are made, of 1.0 ml of the composition per administration, for a total of 300 mg N-vanillyl-10-nonadecynamide administered over a twenty-four hour period.

In the above example, N-vanillyl-9-tetradecynamide, N-vanillyl-6-octadecynamide, N-vanillyl-11-octadecynamide, 12-methyl-N-vanillyl-9-octadecynamide, and 12-ethyl-N-vanillyl-9-octadecynamide are substituted, respectively, for N-vanillyl-10-nonadecynamide, with substantially similar results.

EXAMPLE IV

A composition, according to the instant invention, for parenteral administration, is made with the following components:

| | |
|---|---|
| N—vanillyl-9-octadecynamide | 100 mg/ml of carrier |
| carrier (percent-by-weight): | |
| sesame oil | 98% |
| benzyl alcohol | 2% |

A human subject, weighing 70 kg, is injected via deep-intramuscular injection, with 1.0 ml of the composition prepared above, producing analgesia.

In the above example, N-vanillyl-10-nonadecynamide, N-vanillyl-9-dodecynamide, N-vanillyl-13-dodosynamide, 12-hydroxy-N-vanillyl-9-octadecynamide, N-vanillyl-9-octadecynethioamide, N-[(3,4-dihydroxyphenyl)methyl]-9-octadecynamide, N-[(3-methoxyphenyl)methyl]-6-octadecynamide are substituted, respectively, for N-vanillyl-9-octadecynamide, with substantially similar results.

EXAMPLE V

A composition, according to the instant invention, for parenteral administration, is made by admixing the following components:

| | |
|---|---|
| N—[(4-acetoxy-3-methoxyphenyl)methyl]-9-octadecynamide | 100 mg/ml of carrier |
| carrier (percent by weight): | |
| ethyl oleate | 98.0% |
| benzyl alcohol | 2.0% |

A human subject, weighing 70 kg, is injected via intramuscular injection, with 3.0 ml of the composition prepared above, producing analgesia.

EXAMPLE VI

A composition, according to the instant invention, is made with the following components:

| | |
|---|---|
| N—vanillyl-9-octadecynamide | 20 mg |
| sesame oil | 0.5 ml |

The alkynamide is dissolved in the sesame oil carrier and the solution thus obtained is administered orally to a rat, weighing 100 g, (resulting in a dose of 200 mg per kg) producing analgesia.

EXAMPLE VII

A composition, according to the instant invention, for oral administration, is made with the following components:

| | |
|---|---|
| N—vanillyl-9-octadecynamide | 100 mg/ml of carrier |
| carrier (percent-by-weight): | |
| propylene glycol | 100% |

5.0 ml of the syrup thereby prepared is administered orally to a human subject, producing analgesia.

In the above example, flavoring agents, sweetening agents such as sucrose, lactose, mannitol and saccharin, and preservatives such as glycerin, methyl paraben, propylparaben, benzoic acid, sodium benzoate and alcohol, are added, singly or in combination, to the composition formed above, with substantially similar results.

EXAMPLE VIII

A composition, according to the instant invention, for oral administration, is made with the following components:

| Component | Bulk | Individual Tablet |
| --- | --- | --- |
| N—vanillyl-9-octadecynamide | 100 | 500 mg |
| mannitol | 97.2 | 486 |
| acacia | 5.86 | 29.3 |
| starch | 9.62 | 48.1 |
| talc | 3.2 | 16.0 |
| calcium stearate | 0.42 | 2.1 |
| orange flavor mix | 1.06 | 5.3 |

The above ingredients are admixed into a bulk mixture totalling 17.4 g. Chewable tablets are formed, using tabletting methods known in the art, each containing 1.09 g of the bulk mixture, for a total of 200 tablets formed. A human subject, weighing approximately 70 kg, is orally administered three of the tablets, for a total dose of 1500 mg of alkynamide, producing analgesia.

EXAMPLE IX

A composition, according to the instant invention, for oral administration, is made with the following components:

| N—vanillyl-11-octadecynamide | 1000 mg |
| --- | --- |
| starch | 10.2 |
| magnesium stearate | 5.1 |

A capsule is made by filling with the above ingredients, and administered to a human subject, weighing approximately 70 kg, producing analgesia.

EXAMPLE X

A lotion composition, according to the instant invention, for topical administration, is formed through admixing the following components (percentages-by-weight):

| N—vanillyl-6-octadecynamide | 2.0% |
| --- | --- |
| isopropyl myristate | 8.0% |
| corn oil | 5.0% |
| propylene glycol | 5.0% |
| triethanolamide oleate | 5.0% |
| xanthan gum | 0.5% |
| water | 76.0% |

Approximately 4 ml of the lotion formed is applied to a 80 cm² portion of the skin of a human subject, producing analgesia.

In the above example, N-vanillyl-9-octadecynamide is substituted for N-vanillyl-6-octadecynamide, with substantially similar results.

What is claimed is:

1. Alkynamide compounds and pharmaceutically-acceptable salts thereof, of the formula:

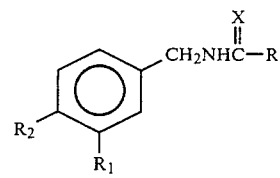

wherein X is O or S; R is straight or branched alkyne having from 11 to 23 carbon atoms; $R_1$ is H, OH or $OCH_3$; $R_2$ is OH or a short-chain ester; and wherein at least one of $R_1$ and $R_2$ is OH or $OCH_3$.

2. Alkynamide compounds, and pharmaceutically-acceptable salts thereof, according to claim 1, wherein $R_1$ is $OCH_3$ and $R_2$ is OH.

3. Alkynamide compounds, and pharmaceutically-acceptable salts thereof, according to claim 1, wherein $R_2$ is a short-chain ester.

4. Alkynamide compounds, and pharmaceutically-acceptable salts thereof, according to claim 2, wherein said alkynamide is N-vanillyl-9-octadecynamide.

5. A composition for producing analgesia in humans or lower animals, comprising:

(a) a safe and effective amount of an alkynamide compound or pharmaceutically-acceptable salt thereof, or mixtures thereof, of the formula:

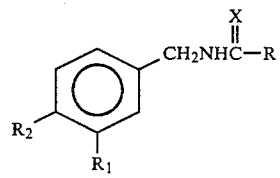

wherein X is O or S, R is straight or branched alkyne having from 11 to 23 carbon atoms, $R_1$ is H, OH, or $OCH_3$, $R_2$ is H, OH or a short-chain ester, and wherein at least one of $R_1$ and $R_2$ is OH or $OCH_3$; and (b) a pharmaceutically-acceptable carrier.

6. A composition, according to claim 5, wherein R is straight or branched alkyne having from 16 to 21 carbon atoms.

7. A composition, according to claim 5, wherein $R_1$ is $OCH_3$ and $R_2$ is OH.

8. A composition according to claim 5, wherein $R_2$ is a short-chain ester.

9. A composition, according to claim 5, comprising a pharmaceutically-acceptable salt of said alkynamide compound, selected from the group consisting of sodium, potassium, calcium, magnesium, and ammonium salts.

10. A composition, according to claim 6, for parenteral administration, comprising at least about 90% by weight of said pharmaceutically-acceptable carrier.

11. A composition, according to claim 6, for oral administration, comprising from about 25% to about 50%, by weight, of said alkynamide.

12. A composition, according to claim 7, for producing analgesia in humans or lower animals, wherein said alkynamide is N-vanillyl-9-octadecynamide.

13. A composition, according to claim 8, wherein said alkynamide is N-[(4-acetoxy-3-methoxyphenyl)methyl]-9-octadecynamide.

14. A method for producing analgesia in humans or lower animals, which comprises administering to said human or lower animal a safe and effective amount of an alkynamide compound or pharmaceutically-acceptable salt thereof, or mixtures thereof, of the formula:

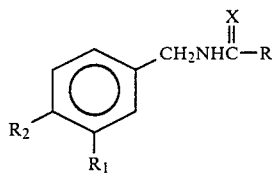

wherein X is O or S; R is straight or branched alkyne having from 11 to 23 carbon atoms; $R_1$ is H, OH, or OCH$_3$; $R_2$ is OH, or a short-chain ester; and wherein at least one of $R_1$ and $R_2$ is OH or OCH$_3$.

15. A method, according to claim 14, wherein R of said alkynamide compound is straight or branched alkyne having from 6 to 21 carbon atoms.

16. A method, according to claim 15, wherein said alkynamide is N-vanillyl-9-octadecynamide.

17. A method, according to claim 15, wherein said alkynamide is administered intramuscularly.

18. A method, according to claim 15, wherein said alkynamide is administered orally.

19. A method, according to claim 15, wherein said alkynamide is administered topically.

* * * * *

UNITED STATES PATENT AND TRADEMARK OFFICE
CERTIFICATE OF CORRECTION

PATENT NO. : 4,532,139
DATED : July 30, 1985
INVENTOR(S) : John M. Janusz and Thomas R. LaHann It is certified that error appears in the above-identified patent and that said Letters Patent are hereby corrected as shown below:

Title, "COMPOUNDS" should read --NOVEL COMPOUNDS--.

Column 1, Title, "COMPOUNDS" should read --NOVEL COMPOUNDS--.

Column 1, line 27, "opoid" should read --opioid--.

Column 1, line 29, "which" should read --with--.

Column 1, Line 43, "Capsicum" should read --<u>Capsicum</u>--.

Column 3, line 47, "alkylnamide" should read --alkynamide--.

Column 5, line 52, "alkynamides" should read --alkynamide--.

Column 8, line 13, "dodosynamide" should read --docosynamide--.

Signed and Sealed this

Eighteenth Day of March 1986

[SEAL]

Attest:

DONALD J. QUIGG

Attesting Officer

Commissioner of Patents and Trademarks